(12) United States Patent
Lacy et al.

(10) Patent No.: US 8,858,887 B2
(45) Date of Patent: Oct. 14, 2014

(54) INTEGRATED CHEMICAL INDICATOR DEVICE

(75) Inventors: Stephen Michael Lacy, Thurmaston (GB); Neil David Tyers, Coalville (GB)

(73) Assignee: Steris, Inc., Temecula, CA (US)

( * ) Notice: Subject to any disclaimer, the term of this patent is extended or adjusted under 35 U.S.C. 154(b) by 1309 days.

(21) Appl. No.: 11/879,987

(22) Filed: Jul. 19, 2007

(65) Prior Publication Data
US 2009/0023217 A1    Jan. 22, 2009

(51) Int. Cl.
*G01N 31/00* (2006.01)
*G01N 31/22* (2006.01)

(52) U.S. Cl.
CPC ............ *G01N 31/228* (2013.01); *G01N 31/005* (2013.01)
USPC .......................................................... 422/85

(58) Field of Classification Search
CPC ....... G01N 31/228; G01N 31/12; G01N 1/22; G01N 31/22; G01N 31/00; G01N 31/005; A61K 48/00; A61K 48/005; C12N 15/1137; C12Q 1/6874; C12Q 1/025; C12Q 1/04; C12Q 1/22
USPC ............................................... 422/85; 436/38
See application file for complete search history.

(56) References Cited

U.S. PATENT DOCUMENTS

| | | | |
|---|---|---|---|
| 4,015,937 A * | 4/1977 | Miyamoto et al. | 436/1 |
| 4,670,385 A * | 6/1987 | Babb et al. | 435/28 |
| 5,169,561 A * | 12/1992 | Gentle et al. | 516/119 |
| 5,518,927 A | 5/1996 | Malchesky et al. | |
| 5,942,438 A | 8/1999 | Antonoplos et al. | |
| 6,063,631 A | 5/2000 | Ignacio | |
| 6,218,189 B1 | 4/2001 | Antonoplos et al. | |
| 6,358,660 B1 | 3/2002 | Agler et al. | |
| 6,635,439 B2 | 10/2003 | Morrison et al. | |
| 6,790,411 B1 | 9/2004 | Read | |
| 7,173,071 B2 | 2/2007 | Suhadolnik et al. | |
| 7,186,373 B2 | 3/2007 | Centanni | |
| 2002/0121629 A1 | 9/2002 | Mikumo et al. | |
| 2003/0211618 A1 * | 11/2003 | Patel | 436/38 |
| 2004/0219057 A1 | 11/2004 | Golden | |
| 2006/0145091 A1 * | 7/2006 | Patel | 250/474.1 |
| 2006/0232735 A1 | 10/2006 | Hokazono et al. | |
| 2008/0057528 A1 * | 3/2008 | Sayre et al. | 435/27 |

FOREIGN PATENT DOCUMENTS

WO    WO 2006/61200 A1    10/2000

* cited by examiner

*Primary Examiner* — Lore Jarrett
(74) *Attorney, Agent, or Firm* — Hudak, Shunk & Farine Co. LPA

(57) ABSTRACT

A chemical indicator device for use in detecting exposure to an oxidizing agent, such as hydrogen peroxide, comprising a substrate or support upon which is disposed a chemical indicator composition (ink) for detecting an oxidizing agent, such as hydrogen peroxide. The chemical indicator composition further comprises an indicator dye that achieves a distinct range of different color changes with clear transitions between colors, upon exposure to different doses of the oxidizing agent, thus allowing for both a qualitative and semi-quantitative assessment of exposure to the agent.

8 Claims, No Drawings

INTEGRATED CHEMICAL INDICATOR DEVICE

FIELD OF THE INVENTION

This invention relates to an indicator device for use in detecting exposure to an oxidizing agent, such a hydrogen peroxide. In particular, this invention relates to an indicator device comprising a substrate or support upon which is disposed a chemical indicator composition (ink) for detecting an oxidizing agent, such as hydrogen peroxide, which achieves a distinct range of different color changes upon exposure to different doses of the oxidizing agent, thus allowing for both qualitative and semi-quantitative assessment of exposure.

BACKGROUND OF THE INVENTION

Chemical and biological indicators for use in detecting exposure to, and the effectiveness of, oxidizing agents are known in the art. In particular, there are a number of known chemical and biological indicators, with respect to hydrogen peroxide detection and efficacy.

Many chemical indicator compositions include, as one component, an indicator dye. For example, U.S. Pat. No. 6,790,411 to Read discloses a hydrogen peroxide indicator that includes a substrate upon which is disposed an indicator composition that includes at least one of a select group of colorants (dyes) that change color and/or become colorless upon exposure to hydrogen peroxide.

As another example, U.S. Pat. No. 6,063,631 to Ignacio also discloses a sterilization indicator that comprises a substrate and an indicator composition to monitor a sterilization process involving hydrogen peroxide vapor. The indicator composition contains a colorant (dye), such as acid fuchsin, that undergoes a color change upon exposure to hydrogen peroxide. The colorant used may be the sole colorant or, optionally, may be combined with a second colorant that does not change color when exposed to hydrogen peroxide.

Both of the foregoing patents disclose a qualitative assessment of exposure to hydrogen peroxide. Neither of these patents discloses a semi-quantitative chemical indicator composition that shows a dose response to hydrogen peroxide over time, i.e., integrated exposure detection. And, while there are a plethora of dyes that have been used in conventional qualitative chemical indicator compositions (inks), few dyes are suitable for use in a semi-quantitative chemical indicator.

Conventional chemical indicator compositions, comprising traditional known dyes, lack the ability to assess the level of exposure to hydrogen peroxide semi-quantitatively, i.e., achieve a distinctive range of color changes responsive to different doses (concentration×time) of an oxidizing agent, such as hydrogen peroxide. Indicators capable of assessing a predetermined number of exposures (total exposure) to an oxidant-type sterilant are known. For example, two patents to Antonoplos et al., i.e., U.S. Pat. Nos. 6,218,189 and 5,942,438, describe metallic azo dyes used to indicate exposure to an oxidant-type sterilant, including hydrogen peroxide. These two patents do not directly involve integrated exposure evaluation. Both disclose a configuration for the metallic azo dye on a metallic surface of a medical instrument, which will change color only after a predetermined number (total) of exposures to a sterilization process. The change of color of the chemical indicator (azo dyes) serves as a warranty indicator or a limited re-use indicator.

Similarly, U.S. Pat. No. 5,518,927 to Malchesky et al. describes a plastic tag comprising a chemical indicator composition. The tag is attached to an instrument, and after repeated exposures, the chemical indicator composition changes color. Based on the color of the indicator, the total number of sterilizations, i.e., uses, that the instrument has undergone, may be determined.

Neither the Antonoplos et al. nor Malchesky et al. patents are directed to the evaluation of the integrated exposure to an oxidizing agent, such as hydrogen peroxide, using a chemical indicator composition in the setting of a single isolated sterilization process or cycle, so that the dose of hydrogen peroxide to which an article is exposed in one setting can be determined.

U.S. Pat. No. 6,635,439 to Morrison et al. is directed to a method for detecting the integrated exposure to hydrogen peroxide of an article in a sterilization chamber having an atmosphere (including VHP). The method comprises the steps of: (a) placing the item into the chamber; (b) placing a substrate capable of absorbing hydrogen peroxide in the chamber; (c) hydrating the substrate in the presence of a thickening agent; (d) on the substrate, reacting hydrogen peroxide with a dye intermediate and an enzyme capable of reacting with hydrogen peroxide to produce a chromophore indicative of the integrated exposure of hydrogen peroxide in the atmosphere; and (e) correlating the chromophore to the integrated exposure of hydrogen peroxide in the atmosphere. The disclosed and claimed preferred dye intermediate comprises a dye-couple of 3-methyl-2-benzothiazoline hydrazone hydrochloride (MBTH) and 3-dimethylaminobenzoic acid (DMAB). The enzyme is a peroxidase. No traditional chemical indicator dyes are disclosed, and the method does not provide for a quick visual read of hydrogen peroxide exposure.

U.S. Pat. No. 7,186,373 to Centanni discloses a method and apparatus for sensing the concentration of a gaseous sterilant in a sealable enclosure. A chemical indicator composition is provided that changes color when exposed to vaporized hydrogen peroxide (VHP). The chemistry of the indicator is adapted to react when exposed to a specific minimum concentration for a specific minimum period of time. The indicator provides a visual determination of whether articles in a sealable enclosure have been exposed to a minimum threshold of vaporized hydrogen peroxide. The indicator comprises a support strip having individual panels upon which incremental gradients of a chemistry, comprising iodide and thiosulfate, are disposed. Each incremental panel in the strip changes color after a different exposure time to a desired average concentration of vaporized hydrogen peroxide.

There is still a need for a chemical indicator composition that can be used to monitor exposure of articles subjected to a sterilization process employing an oxidizing agent, such as hydrogen peroxide, and to provide not only a qualitative assessment of exposure of exposure to an oxidizing agent, but also a semi-quantitative assessment of the integrated exposure of articles to such oxidizing agent. In addition, there is a need for a chemical indicator composition that provides a convenient visual read-out of the semi-quantitative exposure to oxidizing agents that can be used by persons in the field and that does not require resorting to additional, specialized equipment to "read" absorbance or reflectance of an indicator composition upon exposure.

Accordingly, a useful chemical indicator composition should be able to provide not only a qualitative assessment of exposure to an oxidizing agent, but also a semi-quantitative assessment of the dose of sterilant to which an article has been exposed in a single setting or processing, with the dose being determined by the concentration of sterilant multiplied by the time of exposure, without the need to modify the chemistry of the composition in any way or to utilize integrated concentration gradients of chemistries across various areas of a single support. In short, a chemical indicator composition (ink formulation) is needed, which can be uniformly applied to a support and which comprises an indicator dye that achieves distinctive color changes across a wide range of oxidizing-agent doses, with clear transitions between colors achieved, thus allowing for a semi-quantitative assessment of exposure and a reasonable assessment of whether an effective dose or exposure level has been achieved.

It has been discovered that a colorant (dye), specifically pararosaniline base, also known as parafuchsin, unexpectedly demonstrates distinctly different starting point, intermediate and final endpoint colors during exposure to different doses of hydrogen peroxide vapor under both atmospheric and sub-atmospheric conditions, with clear transitions between the colors achieved from the start of exposure to the final or endpoint of the exposure. Related triphenyl methane dyes, such as acid fuchsin, basic fuchsin and new fuchsin, failed to demonstrate any distinctly different intermediate colors during exposure to varying doses of hydrogen peroxide. As such, these related dyes are not suitable for use in semi-quantitative chemical indicators for hydrogen peroxide vapor, as they show little or no distinctive color changes and no clear transitions between color changes, i.e., between the starting color to the endpoint color, upon exposure to hydrogen peroxide vapor over time.

It is an object of this invention to provide a chemical indicator composition, which is also capable and has the added advantage of providing a semi-quantitative assessment of exposure to an oxidizing agent, such as hydrogen peroxide.

It is another object of this invention to provide a chemical indicator composition for monitoring a sterilization process, such as a process using vaporized hydrogen peroxide as a sterilant, which features a visual read-out of the semi-quantitative exposure of articles subjected to the sterilization process.

It is a further object of this invention to provide a semi-quantitative chemical indicator composition for monitoring a sterilization process, which has the advantage of not requiring modification of the chemistry of the composition, or the application of integrated or gradients of the same chemistry, in order to assess semi-quantitative exposure, when the composition is applied to a single support.

It is a further object of this invention to provide a semi-quantitative chemical indicator composition for determining exposure to an oxidizing agent, such as hydrogen peroxide, which advantageously can be used in the field and does not require any additional specialized equipment to "read" a response.

An advantage of the inventive semi-quantitative chemical indicator composition is that it is easy to manufacture, simple to use and accurate.

Yet another advantage of this invention is a semi-quantitative chemical indicator composition that may be used to determine exposure to an oxidizing agent, such as hydrogen peroxide, in decontamination, disinfection, sanitizing, or other cleaning processes and in environments exposed to such processes.

SUMMARY OF THE INVENTION

This invention is directed to a qualitative and semi-quantitative chemical indicator device comprising: a support (substrate) upon which is disposed a chemical indicator composition (ink formulation) one component of which is an indicator dye for assessing integrated exposure to an oxidizing agent, such as hydrogen peroxide.

"Semi-quantitative" means that the chemical indicator composition's dye provides distinctly different color responses to different doses of oxidizing agent, such that exposure can be quantified with a reasonable expectation of accuracy by comparing the color achieved to a pre-calibrated/validated color chart.

"Dose" means the quantity of oxidizing agent to which an object or article is exposed, expressed as a function of concentration over time $[C_s \times t_e]$, where $C_s$ is the concentration of the oxidizing agent (expressed as mg/L or parts per million [ppm], depending on type of application) and $t_e$ is the time of exposure.

In particular, this invention is directed to the use of pararosaniline base as an indicator dye component, which, when incorporated into an ink formulation (chemical indicator composition) and disposed onto a substrate, has been shown to exhibit, upon exposure to an oxidizing agent, such as hydrogen peroxide, under atmospheric and sub-atmospheric conditions for specified time periods, unique and markedly distinct color changes (i.e., from magenta to yellow end point), from the beginning to the end of exposure to an oxidizing agent as well as a series of clearly distinguishable intermediate colors (red, orange, amber), with clear transitions between colors, upon increasing peroxide exposure time. The unexpected ability of the inventive ink composition to show distinct beginning/intermediate/end color changes, with distinct and clear transitions between colors achieved, allows the composition to be calibrated against peroxide dose (hydrogen peroxide vapor exposure over time) under atmospheric and sub-atmospheric conditions.

The invention, as a semi-quantitative chemical indicator for hydrogen peroxide, can provide the user with far more detailed cycle/exposure information than conventional process indicators in the prior art. In addition to confirming and quantifying exposure of an article or object to an oxidizing agent, the invention contemplates (in one embodiment) many duplicate indicator devices placed in different locations within an enclosed or sealed unit and, as such, would find application in mapping hydrogen peroxide exposure (as a dose) in a wide range of enclosed/sealed environments including, but not limited to, sterilizers, isolators, rooms, laboratories, manufacturing facilities, water processing or cycling facilities, food processing equipment, vehicles, and would be quite useful for monitoring the decontamination of large areas.

"Hydrogen peroxide" as used in the description of the invention means and includes all forms of hydrogen peroxide, such as gas, vapor, plasma, aerosolized and the like. The use of the invention is described at times with reference to sterilization units and processes; however, the full scope of the invention is intended to encompass not only use in sterilization units, but also application in any environment where decontamination, disinfection, sanitization, and cleaning occurs and is monitored, including, but not limited to, manufacturing, industry, health care institutions, laboratories, buildings and other enclosed structures, food operations, water cycling/processing, and the like.

DETAILED DESCRIPTION OF THE INVENTION

The inventive chemical indicator device comprises: a support (substrate) and chemical indicator composition (ink composition) further comprising a triphenylmethane dye capable of distinct, different color changes in response to varying doses of an oxidizing agent, such as hydrogen peroxide.

The ink formulation (chemical indicator composition) further comprises a triphenylmethane dye, such as pararosaniline base, a binder, a UV-protectant, an antifoaming agent, a plasticizer, a humectant and one or more solvents for printing/processing. A preferred embodiment comprises pararosaniline base as the dye, since it is capable of producing clearly distinctive, different color changes in response to different doses of hydrogen peroxide. The dye is present in the inventive ink formulations in amounts ranging from about 0.05 to about 10.0 wt. %, based upon the total weight of the ink composition.

Binders may be used in the ink formulations of the invention to facilitate the binding of the ink formulation to a solid support and to provide a supporting matrix for the dye and other components. Useful binders include one or more polymeric resins, preferably a cellulosic polymer, such as nitrocellulose, hydroxypropyl methyl cellulose, ethyl cellulose, and the like. The binder may also comprise a polyamide, polypropylene, polyethylene, polystyrene, polyethylene terephthalate, polyvinyl alcohol, polyvinyl acetate or a mixture of two or more suitable binders. The selection of the binder is not limited and more than one binder may be used. The most important factor in the selection of a binder is that its performance be characterized, i.e., inert or reactive in a known way, with the ink composition or the support upon which the ink composition is disposed. Binders are present in the inventive ink formulations in amounts from about 5% to about 90%, based upon the total weight of the ink formulation.

UV protectants may be used in the ink formulation to inhibit the degradation of the ink formulation, especially the dye, due to exposure to light. Useful UV protectants include benzotriazole-based systems such as mixtures containing, e.g., 2-(2'-hydroxyphenyl)benzotriazole, and derivatives of benzophenone. UV protectants are present in the inventive ink formulations in amounts from about 0.5% to about 5%, based upon the total weight of the ink formulation.

Antifoaming agents may be used in the ink formulation of the invention to reduce foaming of the ink formulation mixture during its manufacture and to improve the printing quality of the resultant ink formulation. Useful antifoaming agents include silicone-based systems such as polydimethylsiloxane. Antifoaming agents are present in the inventive ink formulations in amounts from about 0.01% to about 2%, based upon the total weight of the ink formulation.

Plasticizers and/or humectants may be used in the inventive compositions for improving the flow properties of the ink formulation (smoothness, adhesion power), allowing better processing, enhancing ink performance (humectant), and for improving the flexibility and adhesion of the dried ink formulation, e.g. on a substrate. Useful plasticizers include alkyl esters of phthalic acid such as dioctyl phthalate; useful humectants include glycerol and urea. When used in the inventive compositions, plasticizers are present in amounts from about 0.5% to about 5%, based upon the total weight of the ink formulation. When used in the inventive compositions, humectants are present in amounts from about 0.5% to about 30%, based upon the total weight of the ink formulation.

Generally, in addition to the above components, the chemical indicator composition may include a solvent, which may comprise an organic solvent, water or mixture thereof. Particularly useful organic solvents include alcohols, such as 2-methoxyethanol, 2-ethoxyethanol; other alcohols, such as methanol, ethanol, 1-propanol, 2-propanol, butanols; ketones, such as acetone, methyl ethyl ketone, and esters, such as butyl acetate. A single solvent may be selected, or mixtures of solvents may be used. Solvents, when used, may be selected based upon the support/substrate selected for use in the inventive indicator device, the manufacturing process, or the application for which the inventive device will be used. In some alternative embodiments, no solvent may be necessary in preparing the inventive ink formulations.

In embodiments of the inventive chemical indicator compositions comprising solvents, a suitable solvent should be compatible with the support (substrate) upon which the chemical indicator composition (ink formulation) is placed and should be inert or otherwise not react in an unknown way with any of the components of the ink formulation. The solvent need not dissolve each and every component of the chemical indicator composition (ink formulation). The inventive formulation can be prepared in the form of an aqueous or non-aqueous solution, dispersion or emulsion. Solvent may also be removed from the composition, such as for example, by vacuum or evaporation, leaving the chemical indicator composition as a solid deposit or film layer.

In some alternative embodiments, the chemical indicator composition (ink) may be a solvent-free system, wherein the dye and any additional components are incorporated into suitable resins or waxes known in the art, rather than being dissolved or otherwise dispersed in a solvent.

The chemical indicator composition may also be formulated to be suitable for UV-curing or electron beam curing by combining the dye and any additional components with a suitable vinyl or acrylate monomer (for UV curing), or suitable epoxy resin (for electron beam curing), as is well known in the art.

In use, the chemical indicator composition (ink) is placed upon a support (or substrate) to form the inventive indicator device. Conventional supports/substrates are known in the art. Useful supports include, but are not limited to, polymeric materials, such as polyesters, polystyrenes, polyolefins, polyamides, polymethacrylates and polyvinyl chlorides. In one embodiment, spun-bonded polyolefins provide support for disposition of the ink formulation. There is no requirement that the selected support (substrate) be porous. However, as discussed above, the support (substrate) must be inert or reactive in a known way towards any of the components of the ink formulation, including the solvent.

Generally, the chemical indicator composition may be applied to or disposed/placed upon the substrate/support by any suitable method, including spraying, coating, painting, printing, dipping or immersion. The chemical indicator composition may be placed upon the support as a solid or film layer or be UV-cured or electron beam-cured. The substrate/support may be in the form of a strip, but may also be contained within another carrying or holding device. Conventional strip constructions and structures for containing, carrying or holding supports or substrates are known in the art.

The amount of ink applied to the support is uniform (in chemistry and concentration) across the support. There is no need to alter the chemistry of the ink formulation or to provide for increasing amounts (i.e., a gradient) across the support. The amount of ink uniformly applied may depend on the particular method of application to the support, as different methods may apply ink in a different manner or in a different thickness. In addition, the nature of the substrate/support also has a bearing on the amount of ink applied. For example, a very porous substrate, or a partially reactive substrate, may require more ink to be applied. In all instances, however, the ink content is uniform across the support (substrate).

The support may also include other backing layers, or adhesives, to provide flexibility, adhesion or rigidity. Such layers may be made of polymeric materials, paper, woven fabric or fibers, and non-woven fibers. Layers may be attached in any conventional manner well known to those skilled in the art.

The chemical indicator composition (ink) may itself be in the form of an encapsulated ink, wherein the ink is encapsulated in a transparent polymer to afford abrasion protection, to waterproof the ink, and to enhance user safety from direct exposure to the components of the ink composition. The encapsulant should be permeable or semi-permeable to the oxidizing agent and may also serve as a reaction rate modifier. Suitable encapsulants include polymethacrylate, polyethylene, polyethylene terephthalate, cellophane and polypropylene. An encapsulating layer may be attached to the support (substrate) in any conventional manner well known to those skilled in the art.

The chemical indicator device(s) of the invention may be used for qualitative and/or semi-quantitative monitoring of exposure to oxidizing agents. The unique advantage of the chemical indicator device(s) of the invention is that they comprise a chemical indicator composition (ink formulation) that exhibits a distinct range of several different color changes (from the beginning of the exposure to the end of the exposure), with clear transitions between colors achieved, upon exposure to different doses of oxidizing agents. As such, a correlation can be made between the specific color change achieved and the actual dose of oxidizing agent to which the device is exposed, thus providing a semi-quantitative assessment of the effectiveness of the exposure and/or of the conditions achieved. The key to the invention is the particular indicator dye selected for use in the inventive ink formulations, i.e., pararosaniline base, which unexpectedly provides (from the start of exposure to the end of exposure to an oxidizing agent) a series of color changes with distinctly clear transitions between colors with increasing doses of oxidizing agent.

Qualitatively, a color change means that exposure to the oxidizing agent has occurred. For purposes of the invention, the term "color" may encompass a number of aspects, such as hue, lightness, saturation and the like, where one color may be different from another color if the two colors differ in at least one aspect. The specific color achieved may be compared to a previously calibrated and validated color chart, from which the fact of exposure and the dose to which the device was exposed may be determined.

As discussed above, a key and most advantageous aspect of the invention is that the color changes achieved are distinct and different across varying doses of oxidizing agent, so that a semi-quantitative assessment can also be made by visual comparison to a pre-calibrated/validated color chart. While it is preferable and convenient to employ a visual read out of the color changes achieved, the invention does not preclude the use of equipment to "read" the resultant color achieved, through the determination of reflectance, absorbance, densitometry and the like.

In one embodiment, the chemical indicator device may be placed in an enclosed or sealed environment, such as a sterilizer, with a load of articles being processed. The device may be monitored or observed after processing to assure that the load is exposed to the oxidizing agent and that the dose is effective for sterilization. Thus, the chemical indicator device may be used to evaluate not only if the load was processed by exposure to the oxidizing agent, but also if the processing cycle achieved the appropriate effective conditions, in terms of concentration vs. time, for sterilization. The chemical indicator device may also be useful in conjunction with self-contained biological indicators.

The chemical indicator device may be monitored online or offline. In one embodiment, online monitoring may be performed with liquid, gaseous, plasma or vapor phase oxidizing agents in sterilization processes. In particular, a sterilization process may be performed by placing a load of items along with the chemical indicator device in an enclosed or sealed sterilization process unit. The sterilization process is performed using an oxidizing agent. After the process is completed, the chemical indicator device is observed to see if the chemical indicator composition (ink) has changed colors and the distinct color achieved. If no color change is achieved, or if the color change achieved indicates that the load was exposed to an ineffective or low dose of oxidizing agent, then the concentration of oxidizing agent could be adjusted to achieve the desired dose of oxidizing agent, as reflected in the color change achieved. The load could then be subjected to another processing cycle, with a new indicator to see if the desired conditions are met. The chemical indicator device may also be used off-line to test the oxidizing agent prior to or after performing the sterilization process.

The inventive devices of the invention may also be used in conditions less rigorous than sterilization, such as disinfection, decontamination, sanitizing and cleaning, and/or in other enclosed or sealable environments, such as rooms, laboratories, buildings, clean rooms, vehicles, manufacturing facilities, water/cycling or food or other processing facilities, or any other environments capable of being enclosed or sealed to allow for exposure to an oxidizing agent. In such applications, the inventive chemical indicator device can provide a ready, visual determination of whether exposure has occurred, a minimal dose has been achieved, and/or specific conditions (concentration vs. time) achieved.

The invention may be further illustrated and understood with reference to the following examples. The examples are not intended to limit the scope of the invention in any way, but rather serve to demonstrate specific embodiments and advantages achieved through use of the inventive indicator device.

EXAMPLES

Example 1

Ink Base

Chemical indicator compositions were prepared as follows: an ink base was first prepared (on a 1 liter scale with respect to solvent) by mixing until homogeneous, the components in Table 1.

TABLE 1

| Component | Concentration (by wt. %) |
|---|---|
| 2-Methoxyethanol | 78.15 |
| Ethyl cellulose | 16.81 |
| Benzotriazole-based UV protector | 2.10 |
| Glycerol | 1.68 |
| Dioctyl phthalate | 0.84 |
| Antifoam | 0.42 |

The ink base was divided into 200 g lots. To each 200 g lot was added, with mixing until fully dissolved, one of the dyes listed in Table 2.

TABLE 2

| Component | Quantity (g) | Ink Formulation |
|---|---|---|
| Ink 1 - Acid fuchsin | 0.81 | Ink 1 |
| Ink 2 - New fuchsin | 0.81 | Ink 2 |
| Ink 3 - Basic fuchsin | 0.80 | Ink 3 |
| Ink 4 - Pararosaniline base | 0.81 | Ink 4 |

Example 2

The indicator composition (ink formulation) of Example 1 comprising pararosaniline base [Ink 4] was tested under atmospheric pressure hydrogen peroxide vapor conditions against indicator compositions (ink formulations) comprising individual dyes acid fuchsin [Ink 1], new fuchsin [Ink 2], and basic fuchsin [Ink 3], all of which were added individually to aliquots of the ink base [Table 1].

Each ink formulation was screen printed (as continuous stripes approximately 10 mm wide) on to polypropylene.

Lengths of printed stripes of each ink formulation were cut into approximately 10 mm squares for testing. Up to 20 indicator squares of each ink formulation were placed together face up in a closed chamber with a hydrogen peroxide vapor generator connected to the chamber.

The hydrogen peroxide gassing cycle was started and fractional exposures were achieved by removing one indicator square of each ink formulation periodically over time. The results of cycles run at different hydrogen peroxide vapour concentrations are given in Tables 3-5.

TABLE 3

400 ppm $H_2O_2$ vapor, approx.; Ink Formulations on Polypropylene
Exposure Time (min.)

| Ink | Start color 0 | 3-9 | 15 | 21-27 | 35-50 | 60-80 |
|---|---|---|---|---|---|---|
| Ink 1 | Pink | Pale Pink | Very Pale Pink | Trace Pink | Trace Pink | Colorless |
| Ink 2 | Magenta | Magenta | Magenta | Magenta | Magenta | Magenta |
| Ink 3 | Purple | Purple | Purple | Purple | Purple | Purple |
| Ink 4 | Magenta | Magenta | Red | Pink | Orange | Yellow |

TABLE 4

1300 ppm $H_2O_2$ vapor, approx.; Ink Formulations on Polypropylene
Exposure Time (min.)

| Ink | Start color 0 | 3-9 | 15 | 21-27 | 35-40 | 50-140 |
|---|---|---|---|---|---|---|
| Ink 1 | Pink | Very Pale Pink | Colorless | Colorless | Colorless | Colorless |
| Ink 2 | Magenta | Paler Magenta | Paler Magenta | Paler Magenta | Paler Magenta | Dark Lilac |
| Ink 3 | Purple | Purple | Purple | Purple | Purple | Dark Red |
| Ink 4 | Magenta | Magenta | Red | Orange | Amber | Yellow |

TABLE 5

250 ppm $H_2O_2$ vapor, approx.; Ink Formulations on Polypropylene
Exposure Time (min.)

| Ink | Start color 0 | 3-15 | 21-27 | 35-40 | 50-60 | 80-100 | 120-140 |
|---|---|---|---|---|---|---|---|
| Ink 3 | Purple | Purple | Purple | Purple | Purple | Purple | Purple |
| Ink 4 | Magenta | Magenta | Red | Pink | Orange | Amber | Yellow |

As shown by the results in Tables 3-5, only the inventive composition [Ink 4] provided distinctly different color changes in response to varying doses of hydrogen peroxide.

Example 3

The indicator composition of Example 1 [Ink 4] was tested under low pressure hydrogen peroxide vapor conditions against indicator compositions comprising individual dyes acid fuchsin [Ink 1], new fuchsin [Ink 2], and basic fuchsin [Ink 3] added individually to aliquots of the ink base [Table 1].

Each ink formulation was screen printed (as continuous stripes approximately 10 mm wide) on to polypropylene.

Lengths of printed stripes of each ink formulation were cut into approximately 10 mm squares for testing under low pressure hydrogen peroxide vapor conditions. Indicator squares of each ink formulation were placed into the chamber of a Vaporized Hydrogen Peroxide Biological Indicator Evaluation Resistometer (VHP BIER) vessel and process cycles run where the chamber (internal temperature kept at 50° C.) is evacuated (vacuum pump) prior to the admission of hydrogen peroxide vapor. Table 6 gives the results of exposures of the indicator squares of each ink formulation to different doses of hydrogen peroxide vapor (concentration multiplied by time), expressed as mg/L $H_2O_2$ second.

TABLE 6

Low Pressure $H_2O_2$ Vapor Dose at 50° C.; Ink Formulations on Polypropylene
Dose of Hydrogen Peroxide Vapor (mg/L $H_2O_2$ second)

| Ink | Unprocessed | 10 | 16 | 617 | 685 | 920 |
|---|---|---|---|---|---|---|
| Ink 1 | Pink | Pink | Pink | Very Pale Pink | Colorless | Colorless |
| Ink 2 | Magenta | Magenta | Magenta | Magenta | Magenta | Magenta |
| Ink 3 | Purple | Purple | Purple | Purple | Dark Red | Dark Red |
| Ink 4 | Magenta | Red | Cerise | Orange | Yellow | Yellow |

As shown by the results in Table 6, only the inventive composition [Ink 4] provided distinctly different color changes in response to varying doses of hydrogen peroxide at sub-atmospheric pressures.

Example 4

A chemical indicator composition was prepared by mixing until homogeneous, the components in Table 7.

TABLE 7

INK 5

| Component | Concentration (by wt. %) |
|---|---|
| 2-Methoxyethanol | 78.24 |
| Ethyl cellulose | 16.82 |
| Benzotriazole-based UV protector | 2.10 |
| Dioctyl phthalate | 2.10 |
| Antifoam | 0.42 |
| Pararosaniline base | 0.31 |

This chemical indicator composition, Ink 5, was screen printed (as continuous stripes approximately 10 mm wide) on to self-adhesive spun-bonded polyolefin having a glassine backing (and acrylic adhesive).

This chemical indicator composition, Ink 5, was also screen printed (as continuous stripes approximately 10 mm wide) on to polypropylene and the ink stripe encapsulated by overlaminating with a cellophane laminate using an acrylic adhesive.

Example 5

Sections of printed stripes of each ink formulation were cut into approximately 30-50 mm long indicators for testing under low pressure hydrogen peroxide vapor conditions. Indicators of ink formulation Ink 5 (Table 7) printed on to each substrate (as described in Example 4) were placed into the chamber of a Vaporized Hydrogen Peroxide Biological Indicator Evaluation Resistometer (VHP BIER) vessel and process cycles run where the chamber (internal temperature kept at 50° C.) is evacuated (vacuum pump) prior to the admission of hydrogen peroxide vapor. Table 8 gives the results of exposures of the chemical indicator composition, Ink 5, on each substrate, to different doses of hydrogen peroxide vapor (concentration multiplied by time), expressed as mg/L $H_2O_2$ second.

TABLE 8

Low Pressure $H_2O_2$ Vapor Dose at 50° C.; Ink 5 on Polypropylene and Self-adhesive Spun-bonded Polyolefin

| Ink | Substrate | Dose of Hydrogen Peroxide Vapour (mg/L $H_2O_2$ second) | | |
|---|---|---|---|---|
| | | Unprocessed | 19 | 737 |
| Ink 5 | Polypropylene | Magenta | Red | Yellow |
| Ink 5 | Self-adhesive spun-bonded polyolefin | Magenta | Gold | Yellow |

As shown by the results in Table 8, the inventive composition [ink 5] provided distinctly different color changes on different substrates in response to varying doses of hydrogen peroxide at sub-atmospheric pressures.

In accordance with the patent statutes, the best mode and preferred embodiment have been set forth; the scope of the invention is not limited thereto, but rather by the scope of the attached claims.

What is claimed is:

1. A chemical indicator device for monitoring the effectiveness of a sterilization process that uses an oxidizing agent as a sterilant and for semi-quantitatively assessing exposure to the oxidizing agent, consisting of:
   a. a substrate; and
   b. a chemical indicator composition uniformly disposed upon the substrate, consisting of a single dye, pararosaniline base, which when reacted directly with the oxidizing agent sterilant, achieves a range of different, distinct color changes over time in response to direct exposure to different doses of the oxidizing agent sterilant during a single sterilization cycle,
   wherein the colors achieved by the pararosaniline base are compared to a pre-calibrated, visual color chart so that a semi-quantitative assessment of the dose of the oxidizing agent sterilant to which the device was exposed during the sterilization cycle can he made.

2. The device according to claim 1, wherein the substrate consists of one or more polymeric materials, paper, woven fibers, non-woven fibers, or a combination of two or more thereof.

3. The device according to claim 2, wherein the polymeric material is selected from the group consisting of polyesters, polystyrenes, polyolefins, polyamides, polymethacrylates, polyvinyl chlorides and mixtures thereof.

4. The device according to claim 3, wherein the polymeric material is spun bonded polyolefin.

5. The device according to claim 1, wherein the oxidizing agent sterilant being assessed by the device is hydrogen peroxide.

6. The device according to claim 1, wherein the dose of the oxidizing agent to which the pararosaniline base is exposed at any given point in time in a single sterilization cycle is determined by multiplying a known concentration of the oxidizing agent by the time of exposure of the pararosaniline base to the oxidizing agent.

7. The chemical indicator device according to claim 1, further consisting of the pre-calibrated, visual color chart for use in making a semi-quantitative assessment of the dose of the oxidizing agent sterilant to which the device was exposed.

8. A method of monitoring the effectiveness of a sterilization process that utilizes an oxidizing agent as a sterilant and of determining, semi-quantitatively, exposure to the oxidizing agent, comprising the steps of:
   a. providing a chemical indicator device comprising a chemical indicator composition uniformly disposed on a support, wherein the composition consists of a single dye, pararosaniline base, which itself achieves different, distinct color changes over time in response to exposure to different doses of the oxidizing agent sterilant;
   b. placing the device into a sterilizing environment wherein the dye will be directly exposed to the oxidizing agent sterilant; and
   c. comparing the color change achieved by the dye at any point in time during a sterilization cycle to a pre-calibrated, visual color chart to assess the dose of oxidizing agent sterilant to which the chemical indicator composition was exposed.

* * * * *